US011427872B2

(12) United States Patent
Taniuchi

(10) Patent No.: US 11,427,872 B2
(45) Date of Patent: Aug. 30, 2022

(54) MARKER FOR PANCREATIC CANCER AND INTRADUCTAL PAPILLARY MUCINOUS NEOPLASMS

(71) Applicant: NATIONAL UNIVERSITY CORPORATION KOCHI UNIVERSITY, Kochi (JP)

(72) Inventor: Keisuke Taniuchi, Kochi (JP)

(73) Assignee: NATIONAL UNIVERSITY CORPORATION KOCHI UNIVERSITY, Kochi (JP)

(*) Notice: Subject to any disclaimer, the term of this patent is extended or adjusted under 35 U.S.C. 154(b) by 379 days.

(21) Appl. No.: 16/060,735

(22) PCT Filed: Nov. 22, 2016

(86) PCT No.: PCT/JP2016/084537
§ 371 (c)(1),
(2) Date: Jun. 8, 2018

(87) PCT Pub. No.: WO2017/098915
PCT Pub. Date: Jun. 15, 2017

(65) Prior Publication Data
US 2018/0355440 A1    Dec. 13, 2018

(30) Foreign Application Priority Data
Dec. 11, 2015 (JP) .............................. JP2015-242679

(51) Int. Cl.
| G01N 33/574 | (2006.01) |
| C12Q 1/6886 | (2018.01) |
| C12N 15/09 | (2006.01) |
| C07K 14/47 | (2006.01) |
| C07K 16/30 | (2006.01) |

(52) U.S. Cl.
CPC .......... *C12Q 1/6886* (2013.01); *C07K 14/47* (2013.01); *C12N 15/09* (2013.01); *G01N 33/57438* (2013.01); *C07K 16/303* (2013.01); *C12Q 2600/106* (2013.01); *C12Q 2600/112* (2013.01); *C12Q 2600/118* (2013.01); *C12Q 2600/156* (2013.01); *C12Q 2600/158* (2013.01)

(58) Field of Classification Search
CPC .......... C12Q 1/6886; C12Q 2600/118; C12Q 2600/158; G01N 33/57438; C07K 16/303
See application file for complete search history.

(56) References Cited

U.S. PATENT DOCUMENTS

| 7,282,207 | B1 | 10/2007 | Colpitts et al. |
| 2006/0294607 | A1 | 12/2006 | Fitzhugh et al. |
| 2012/0070853 | A1* | 3/2012 | Johansen ......... G01N 33/57419 435/7.92 |
| 2012/0121602 | A1 | 5/2012 | Sandler et al. |
| 2012/0219548 | A1* | 8/2012 | Jirstrom ............. C07K 16/3046 424/133.1 |
| 2014/0121153 | A1 | 5/2014 | Sandler et al. |
| 2015/0111758 | A1 | 4/2015 | Sorlie et al. |
| 2016/0083445 | A1 | 3/2016 | Sandler et al. |

FOREIGN PATENT DOCUMENTS

| JP | 2013-27387 | 2/2013 |
| JP | 2015-212302 | 11/2015 |
| WO | WO-9952942 A2 * | 10/1999 ........... C12Q 1/6827 |

OTHER PUBLICATIONS

Larsson et al., Diagnostic Pathology, 2013, 8: 109, pp. 1-7.*
Dallas et al., Am J Physiol Cell Physiol, 303: C616-624. (Year: 2012).*
Hacker et al. Gut, 40: 623-627. (Year: 1997).*
Pennisi, Science, 281(5384): 1787-1789. (Year: 1998).*
Gronborg et al., Biomarker Discovery from Pancreatic Cancer Secretome Using a Differential Proteomic Approach, Mol. Cell. Proteomics, 2006, 5:157-171.*
Partial Supplementary European Search Report dated May 15, 2019 in corresponding European Application No. 16872815.2.
International Search Report dated Feb. 28, 2017 in International (PCT) Application No. PCT/JP2016/084537.
Ney et al., "Podocalyxin-like protein 1 expression is useful to differentiate pancreatic ductal adenocarcinomas from adenocarcinomas of the biliary and gastrointestinal tracts", Human Pathology, vol. 38, 2007, p. 359-364.
Taniuchi et al., "Toward the establishment of a new method for diagnosing pancreatic cancer using mRNA derived from exosome of a pancreatic cancer cell in serum", The Journal of Japan Pancreas Society, vol. 30, No. 3, 2015, p. 262, with English translation.
Office Action dated Mar. 2, 2022 in Australian Patent Application No. 2021202237, 3 pages.
Saukkonen et al., "Podocalyxin Is a Marker of Poor Prognosis in Pancreatic Ductal Adenocarcinoma", PLOS ONE, 2015, vol. 10, No. 6, e0129012, pp. 1-15, 15 pages.

* cited by examiner

*Primary Examiner* — Hong Sang
(74) *Attorney, Agent, or Firm* — Wenderoth, Lind & Ponack, L.L.P.

(57) ABSTRACT

A marker having excellent sensitivity and specificity to pancreatic cancer and intraductal papillary mucinous neoplasms. Also, a kit for diagnosing pancreatic cancer and intraductal papillary mucinous neoplasms to detect the marker, and a method for evaluating a metastasis of a pancreas cancer cell by using the marker. The marker for pancreatic cancer and intraductal papillary mucinous neoplasms according to the present invention comprises one or more proteins selected from the group essentially consisting of secretoglobin, family 1D, member 2 and podocalyxin-like protein. The kit for diagnosing pancreatic cancer and intraductal papillary mucinous neoplasms according comprises an antibody to one or more proteins selected from the group essentially consisting of secretoglobin, family 1D, member 2 and podocalyxin-like protein.

5 Claims, 14 Drawing Sheets

Specification includes a Sequence Listing.

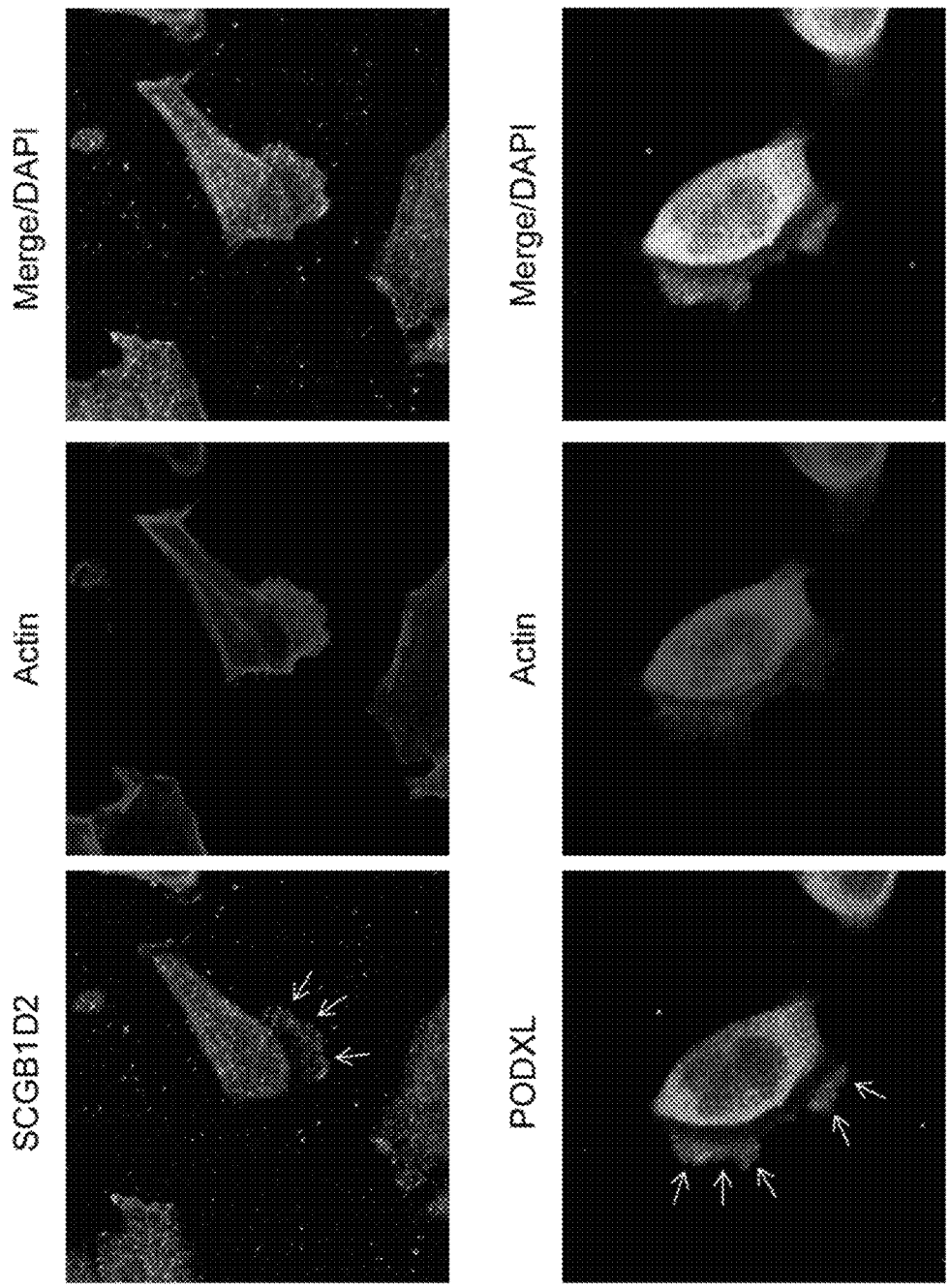
[Fig.1]

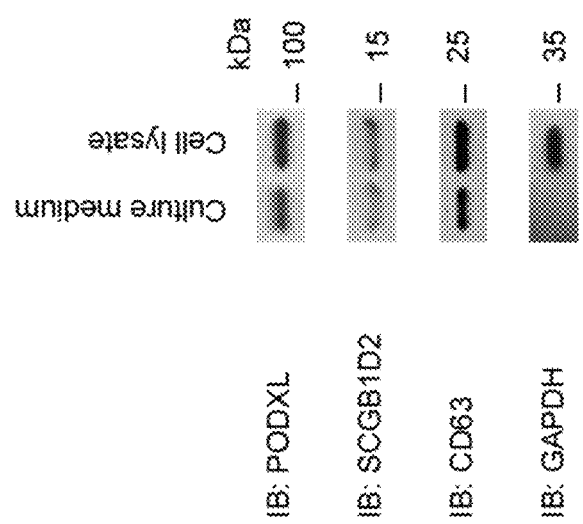
[Fig.2]

[Fig.3]
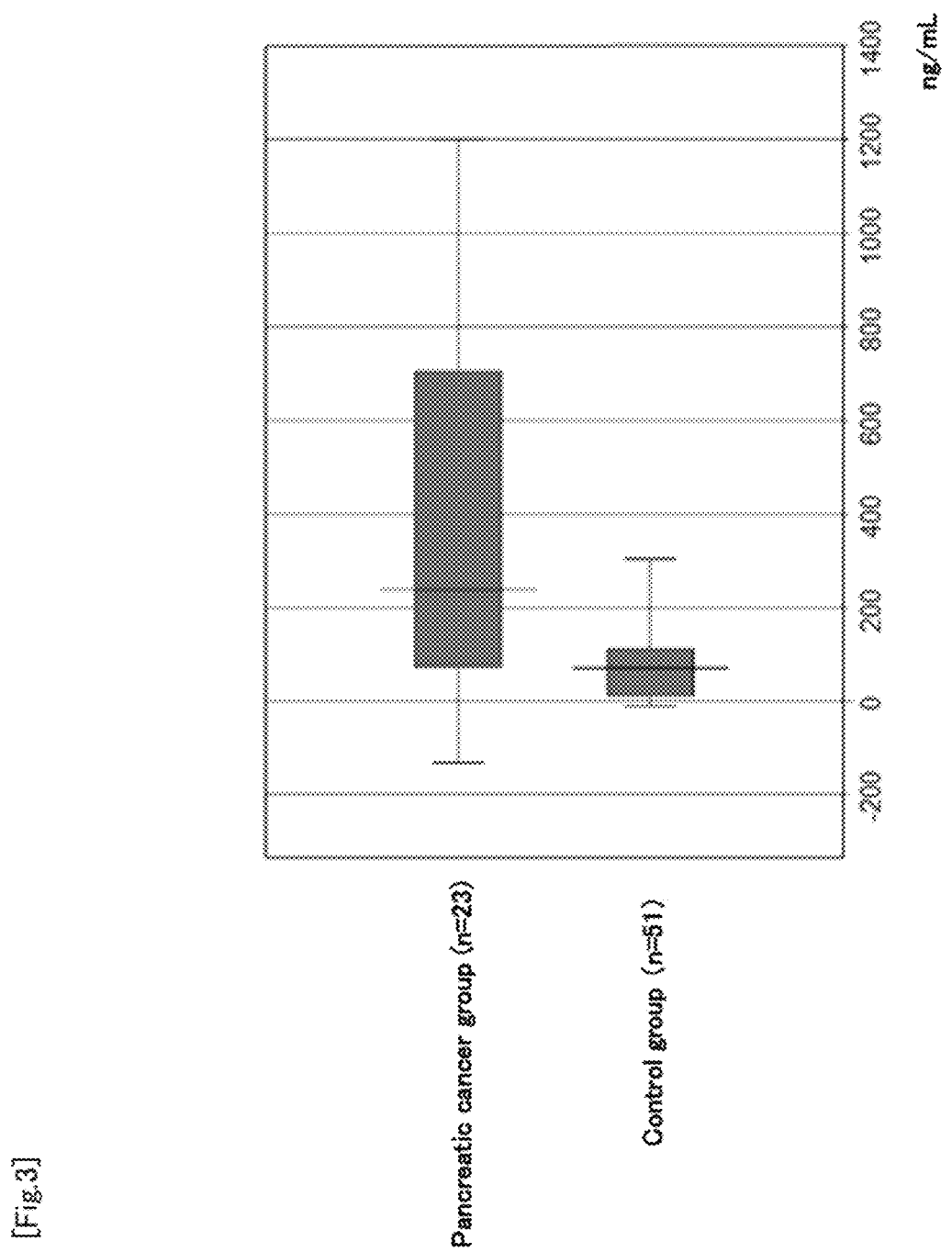

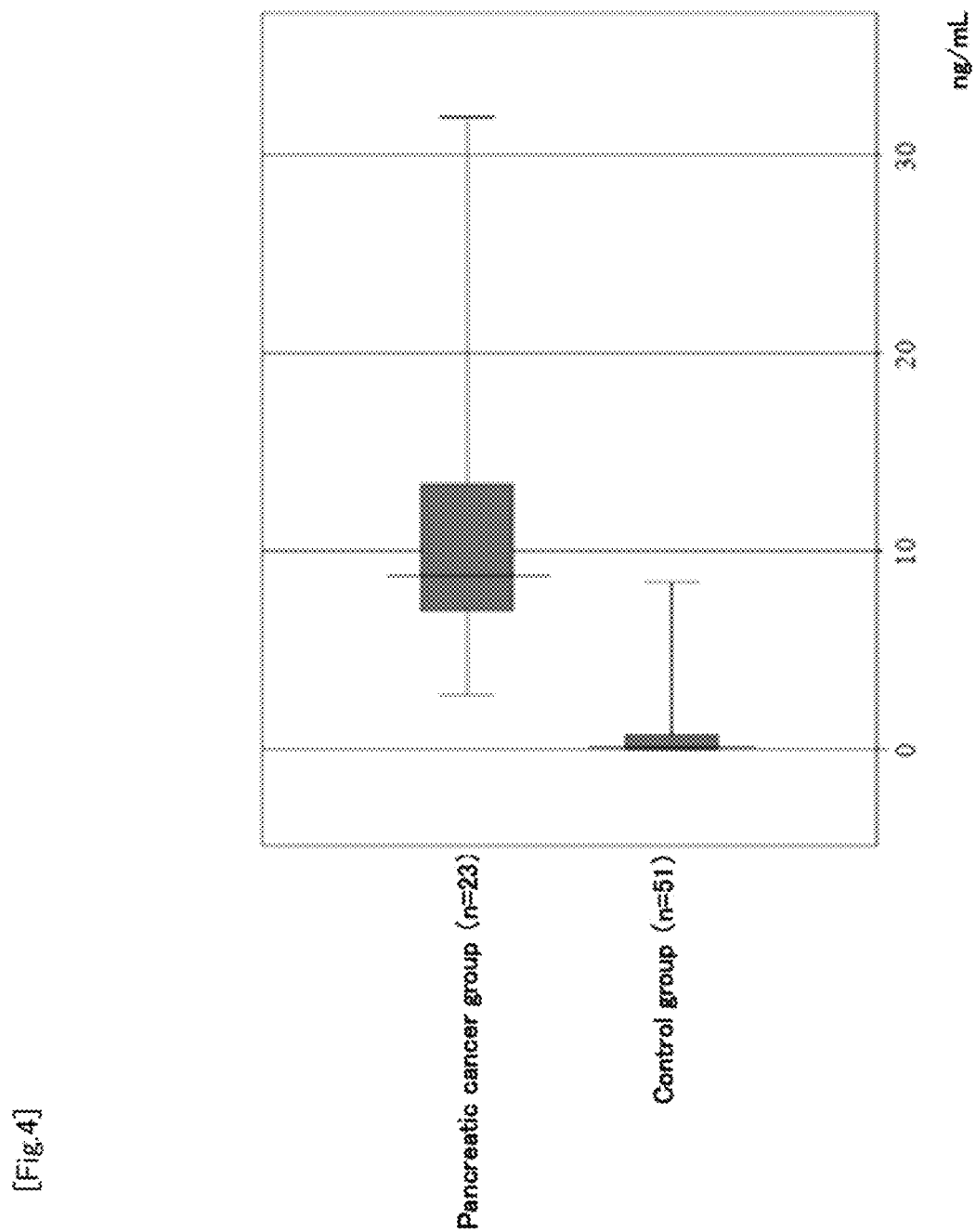
[Fig.4]

[Fig.5]
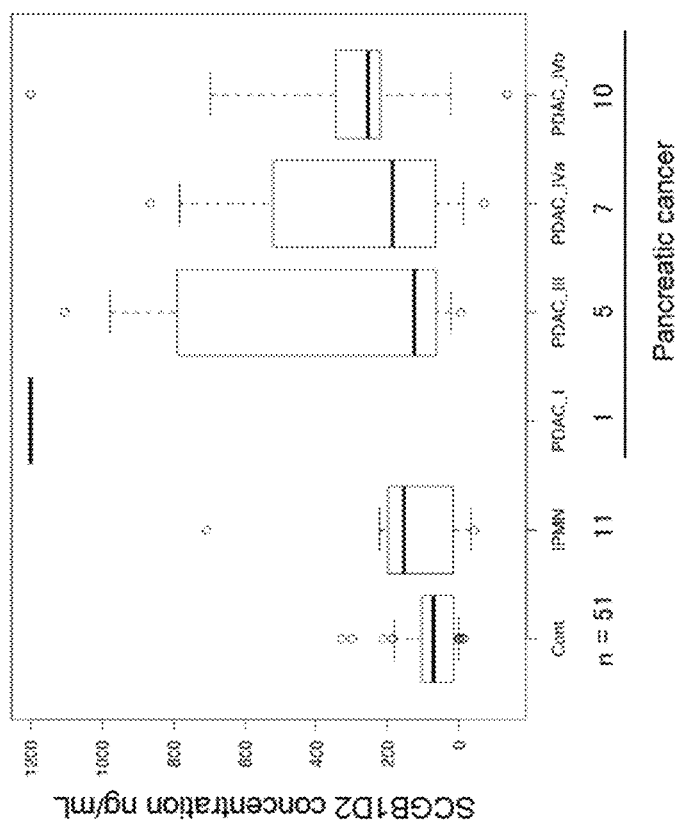

[Fig.6]
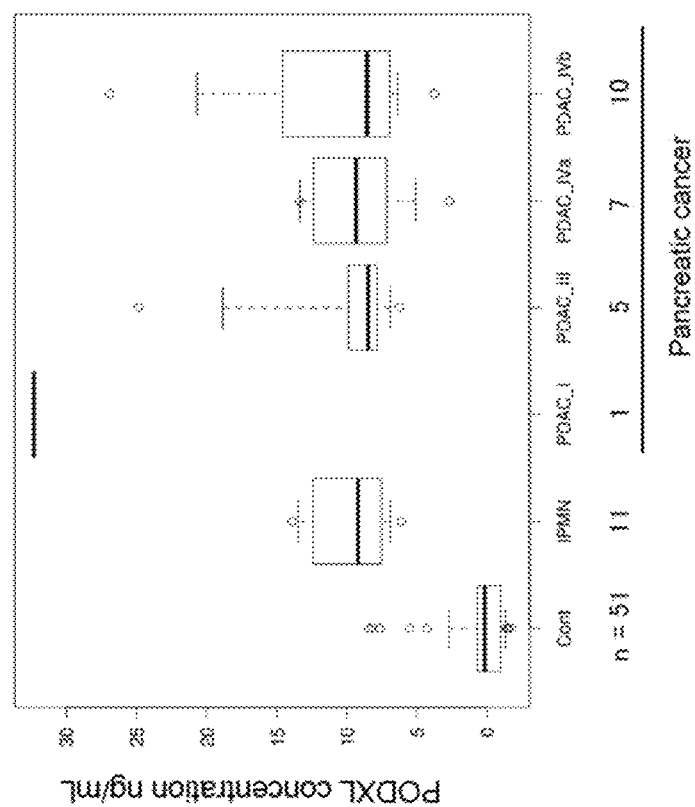

[Fig. 7]
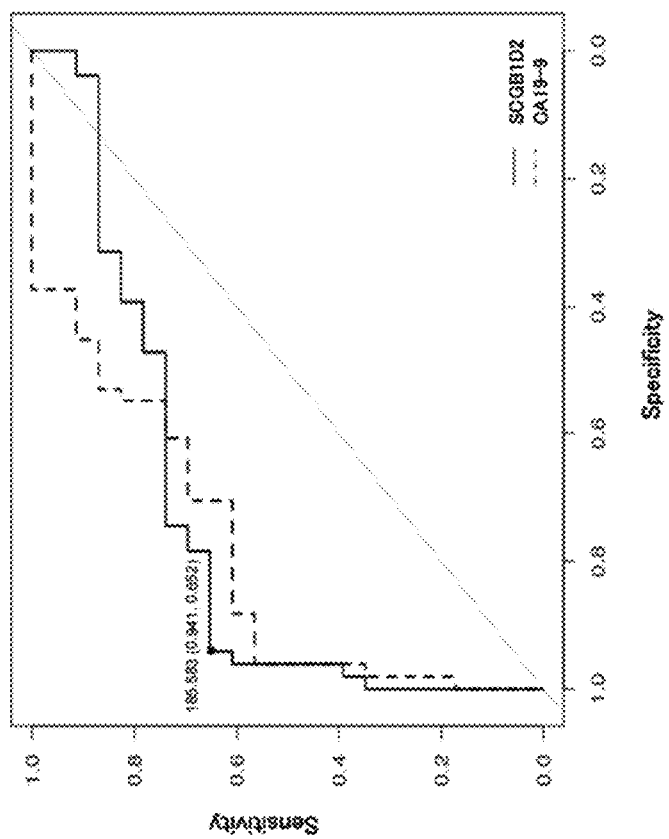

[Fig. 8]
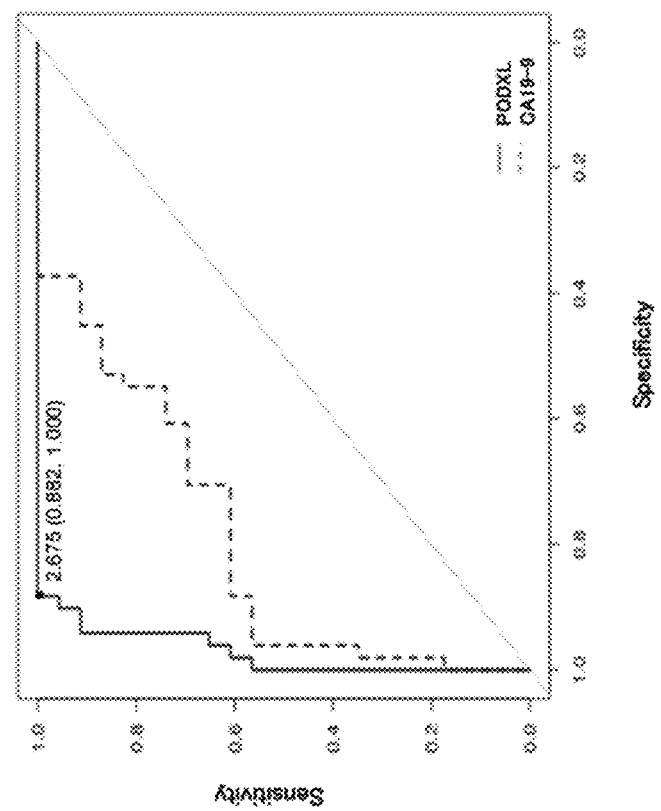

[Fig. 9]
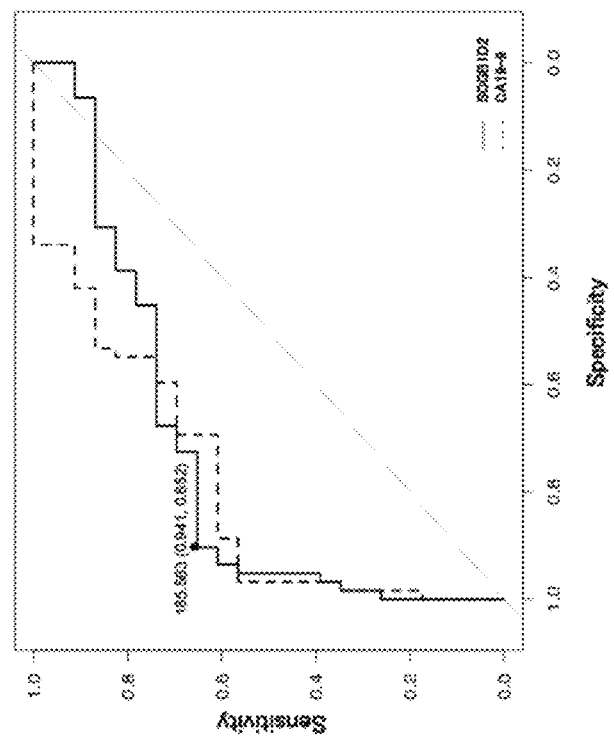

[Fig. 10]
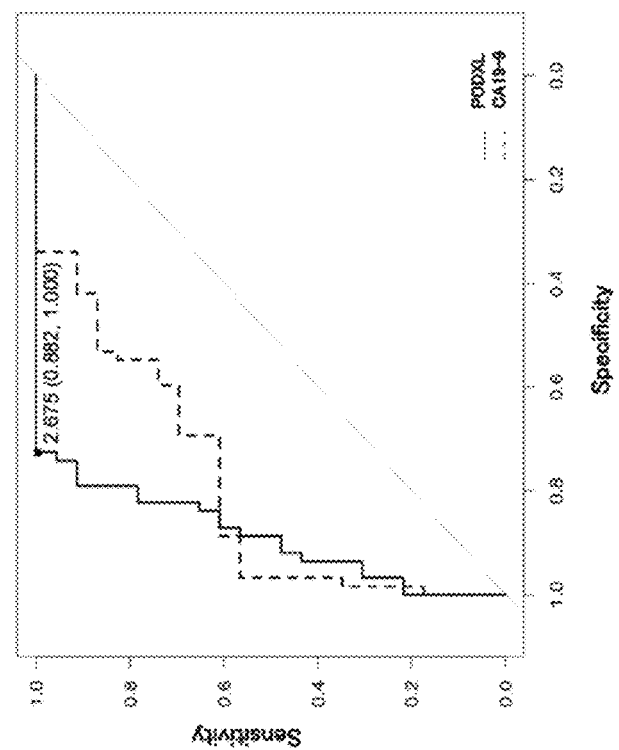

[Fig.11]
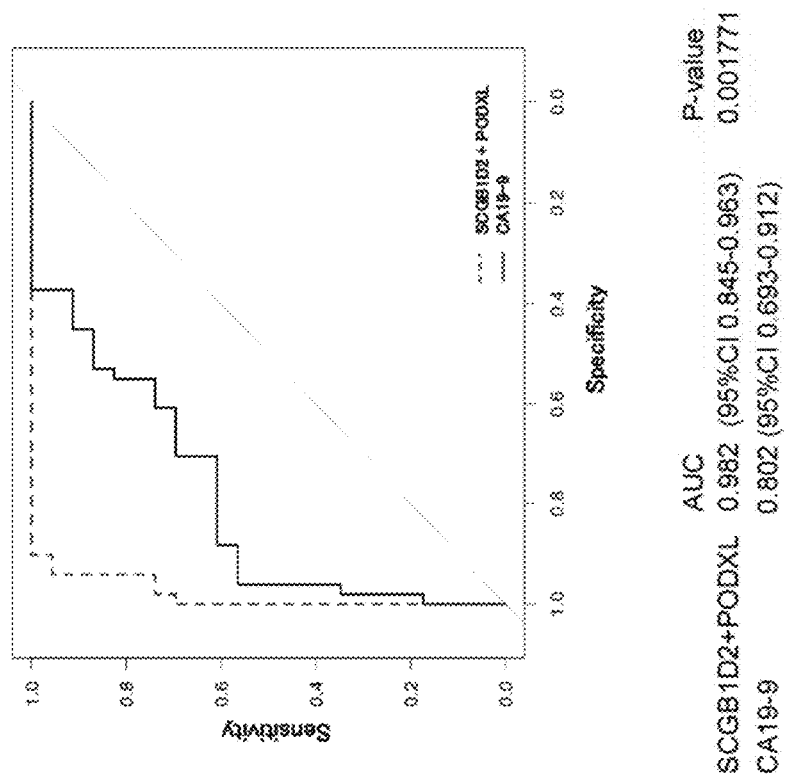

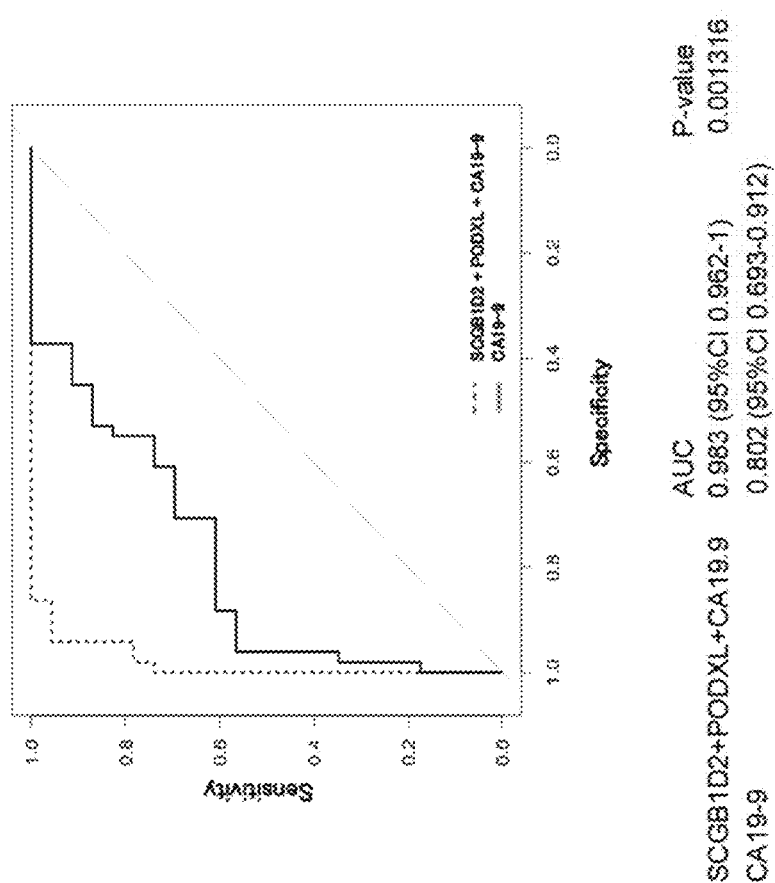
[Fig.12]

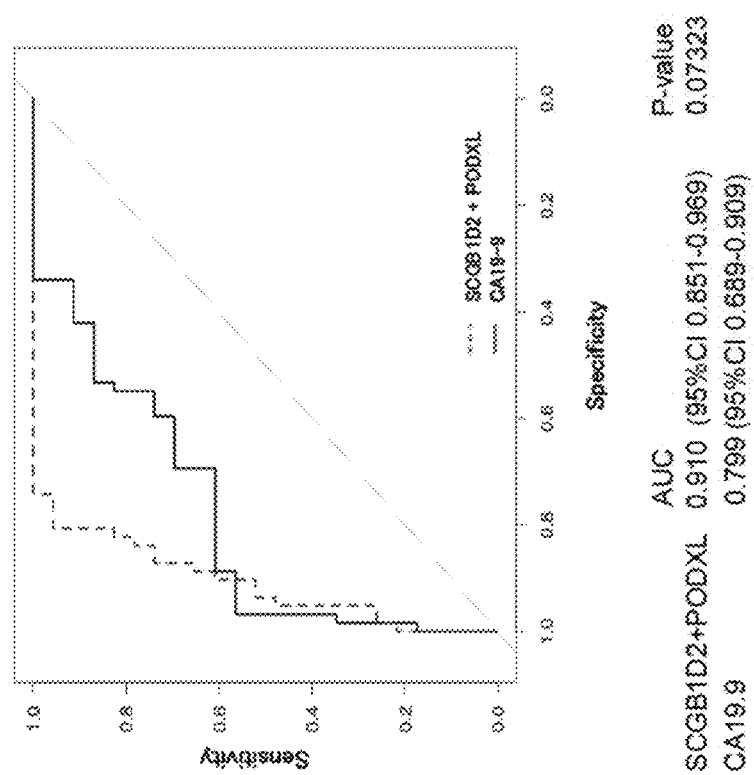
[Fig.13]

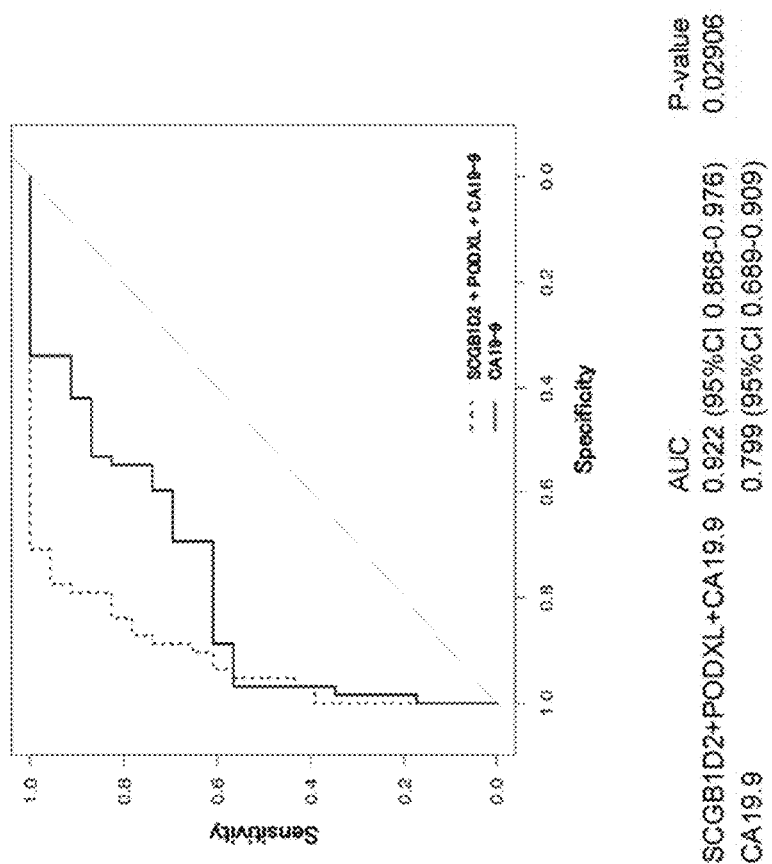
[Fig.14]

SEQUENCE LISTING

```
<160> NUMBER OF SEQ ID NOS: 2

<210> SEQ ID NO 1
<211> LENGTH: 90
<212> TYPE: PRT
<213> ORGANISM: Homo sapiens

<400> SEQUENCE: 1

Met Lys Leu Ser Val Cys Leu Leu Leu Val Thr Leu Ala Leu Cys Cys
                 5                  10                  15

Tyr Gln Ala Asn Ala Glu Phe Cys Pro Ala Leu Val Ser Glu Leu Leu
             20                  25                  30

Asp Phe Phe Phe Ile Ser Glu Pro Leu Phe Lys Leu Ser Leu Ala Lys
         35                  40                  45

Phe Asp Ala Pro Pro Glu Ala Val Ala Lys Leu Gly Val Lys Arg
     50                  55                  60

Cys Thr Asp Gln Met Ser Leu Gln Lys Arg Ser Leu Ile Ala Glu Val
 65                  70                  75                  80

Leu Val Lys Ile Leu Lys Lys Cys Ser Val
                 85                  90

<210> SEQ ID NO 2
<211> LENGTH: 558
<212> TYPE: PRT
<213> ORGANISM: Homo sapiens

<400> SEQUENCE: 2

Met Arg Cys Ala Leu Ala Leu Ser Ala Leu Leu Leu Leu Leu Ser Thr
                 5                  10                  15

Pro Pro Leu Leu Pro Ser Ser Pro Ser Pro Ser Pro Ser Pro Ser Gln
             20                  25                  30

Asn Ala Thr Gln Thr Thr Thr Asp Ser Ser Asn Lys Thr Ala Pro Thr
         35                  40                  45

Pro Ala Ser Ser Val Thr Ile Met Ala Thr Asp Thr Ala Gln Gln Ser
     50                  55                  60

Thr Val Pro Thr Ser Lys Ala Asn Glu Ile Leu Ala Ser Val Lys Ala
 65                  70                  75                  80

Thr Thr Leu Gly Val Ser Ser Asp Ser Pro Gly Thr Thr Leu Ala
                 85                  90                  95

Gln Gln Val Ser Gly Pro Val Asn Thr Thr Val Ala Arg Gly Gly Gly
             100                 105                 110

Ser Gly Asn Pro Thr Thr Thr Ile Glu Ser Pro Lys Ser Thr Lys Ser
         115                 120                 125

Ala Asp Thr Thr Thr Val Ala Thr Ser Thr Ala Thr Ala Lys Pro Asn
     130                 135                 140

Thr Thr Ser Ser Gln Asn Gly Ala Glu Asp Thr Thr Asn Ser Gly Gly
145                 150                 155                 160
```

-continued

```
Lys Ser Ser His Ser Val Thr Thr Asp Leu Thr Ser Thr Lys Ala Glu
            165                 170                 175

His Leu Thr Thr Pro His Pro Thr Ser Pro Leu Ser Pro Arg Gln Pro
            180                 185                 190

Thr Ser Thr His Pro Val Ala Thr Pro Thr Ser Ser Gly His Asp His
            195                 200                 205

Leu Met Lys Ile Ser Ser Ser Ser Thr Val Ala Ile Pro Gly Tyr
            210                 215                 220

Thr Phe Thr Ser Pro Gly Met Thr Thr Thr Leu Leu Glu Thr Val Phe
225                 230                 235                 240

His His Val Ser Gln Ala Gly Leu Glu Leu Leu Thr Ser Gly Asp Leu
            245                 250                 255

Pro Thr Leu Ala Ser Gln Ser Ala Gly Ile Thr Ala Ser Ser Val Ile
            260                 265                 270

Ser Gln Arg Thr Gln Gln Thr Ser Ser Gln Met Pro Ala Ser Ser Thr
            275                 280                 285

Ala Pro Ser Ser Gln Glu Thr Val Gln Pro Thr Ser Pro Ala Thr Ala
            290                 295                 300

Leu Arg Thr Pro Thr Leu Pro Glu Thr Met Ser Ser Ser Pro Thr Ala
305                 310                 315                 320

Ala Ser Thr Thr His Arg Tyr Pro Lys Thr Pro Ser Pro Thr Val Ala
            325                 330                 335

His Glu Ser Asn Trp Ala Lys Cys Glu Asp Leu Glu Thr Gln Thr Gln
            340                 345                 350

Ser Glu Lys Gln Leu Val Leu Asn Leu Thr Gly Asn Thr Leu Cys Ala
            355                 360                 365

Gly Gly Ala Ser Asp Glu Lys Leu Ile Ser Leu Ile Cys Arg Ala Val
            370                 375                 380

Lys Ala Thr Phe Asn Pro Ala Gln Asp Lys Cys Gly Ile Arg Leu Ala
385                 390                 395                 400

Ser Val Pro Gly Ser Gln Thr Val Val Lys Glu Ile Thr Ile His
            405                 410                 415

Thr Lys Leu Pro Ala Lys Asp Val Tyr Glu Arg Leu Lys Asp Lys Trp
            420                 425                 430

Asp Glu Leu Lys Glu Ala Gly Val Ser Asp Met Lys Leu Gly Asp Gln
            435                 440                 445

Gly Pro Pro Glu Glu Ala Glu Asp Arg Phe Ser Met Pro Leu Ile Ile
            450                 455                 460

Thr Ile Val Cys Met Ala Ser Phe Leu Leu Leu Val Ala Ala Leu Tyr
465                 470                 475                 480

Gly Cys Cys His Gln Arg Leu Ser Gln Arg Lys Asp Gln Gln Arg Leu
            485                 490                 495

Thr Glu Glu Leu Gln Thr Val Glu Asn Gly Tyr His Asp Asn Pro Thr
            500                 505                 510

Leu Glu Val Met Glu Thr Ser Ser Glu Met Gln Glu Lys Lys Val Val
            515                 520                 525

Ser Leu Asn Gly Glu Leu Gly Asp Ser Trp Ile Val Pro Leu Asp Asn
            530                 535                 540

Leu Thr Lys Asp Asp Leu Asp Glu Glu Asp Thr His Leu
545                 550                 555
```

MARKER FOR PANCREATIC CANCER AND INTRADUCTAL PAPILLARY MUCINOUS NEOPLASMS

TECHNICAL FIELD

The present invention relates to a marker having excellent sensitivity and specificity to pancreatic cancer and intraductal papillary mucinous neoplasms, a kit for diagnosing pancreatic cancer and intraductal papillary mucinous neoplasms to detect the marker, and a method for evaluating a metastasis of a pancreas cancer cell by using the marker.

BACKGROUND ART

The term "tumor" means a cell which abnormally proliferates and a state in which such a cell continues to proliferate even if the cause of such abnormal proliferation is eliminated or removed. A benign tumor among tumors slowly grows and do not develop metastasis; therefore, in general, there is no problem if a benign tumor is removed, and even if left untreated, a benign tumor is not life-threatening. On the one hand, a malignant tumor, i.e. cancer, rapidly grows unlike a benign tumor, and also metastasizes to lymph nodes and other organs to grow. Thus, for example, even if a malignant tumor is removed by surgical operation, cancer cells that have remained even slightly or cancer cells that have already metastasized to lymph nodes or other organs may start growing proliferously again. Thus, a cancer patient has a poor prognosis after treatment is completed, and a survival rate after 5 years in each cancer is investigated. In general, a cancer is finally considered to be cured when a patient does not experience a recurrence of a cancer after 5 years since a cancer was deemed to have disappeared by treatment.

Pancreatic cancer is said to have the worst prognosis among cancers. The reason is that it is difficult to detect pancreatic cancer in an early stage, since the pancreas is a retroperitoneal organ. In addition, the mobility of a pancreatic cancer cell is extremely high, so even a small pancreatic cancer of, for example, 2 cm or less immediately infiltrates a circumferential blood vessel, gastrointestinal tract, nerve and so on, metastasizes to a surrounding lymph node, and develops distant metastasis to the liver and the like. It is therefore very important to evaluate the progression of pancreatic cancer.

Although a biopsy is accurate to diagnose cancer, a biopsy gives a patient a pain. Thus, in general, an examination using a cancer marker is preliminarily performed. A cancer marker is a substance that is specifically produced by cancer in a living body, and the progress of cancer can be evaluated by measuring the amount thereof in the body fluid. For example, as a pancreatic cancer marker, CA 19-9, which is an abnormal sugar chain and which is specifically produced in a cancer cell, has been used for about 30 years, and a pancreatic cancer marker that is superior to CA 19-9 has not been practically used yet.

On the one hand, particularly in the diagnosis of pancreatic cancer in an early stage, CA 19-9 has a problem of low sensitivity and low usefulness. Thus, a superior cancer marker is being searched. For example, Patent document 1 discloses the specific protein as a pancreatic cancer marker.

PRIOR ART DOCUMENT

Patent Document

Patent document 1: JP 2013-027387 A

DISCLOSURE OF THE INVENTION

Problems to be Solved by the Invention

As described above, CA 19-9 is in actual clinical use as a pancreatic cancer marker, but CA 19-9 is particularly insensitive to pancreatic cancer in an early stage, so that an alternative pancreatic cancer marker for CA 19-9 has been required.

Also, there is a disease called intraductal papillary mucinous neoplasm, i.e., IPMN. If IPMN is left untreated, IPMN transforms into malignancy. It is therefore necessary to surgically remove IPMN at the stage of adenoma, but there is not a serodiagnostic marker for IPMN and a serum concentration of CA 19-9 often does not increase in an IPMN patient. Thus, it is also required to develop a serodiagnostic marker for IPMN.

Under the above-described circumstances, the objective of the present invention is to provide a marker having excellent sensitivity and specificity to pancreatic cancer and intraductal papillary mucinous neoplasms. Also, the objective of the present invention is to provide a kit for diagnosing pancreatic cancer and intraductal papillary mucinous neoplasms to detect the marker, and method for evaluating a metastasis of a pancreas cancer cell by using the marker.

Means for Solving the Problems

The inventor of the present invention made extensive studies to solve the above problems. As a result, the inventor completed the present invention by identifying secretoglobin, family 1D, member 2 and podocalyxin-like protein as glycoproteins which accumulate in a lamellipodium, which is essential for an invasion of a pancreas cancer cell, and by finding that the glycoproteins are useful as a pancreas cancer marker, since the glycoproteins are released from a pancreas cancer cell to the outside of the cell and the glycoproteins are also useful as a marker of intraductal papillary mucinous neoplasms.

Hereinafter, the present invention is described.

[1] A marker for pancreatic cancer and intraductal papillary mucinous neoplasms, comprising one or more proteins selected from the group essentially consisting of secretoglobin, family 1D, member 2 and podocalyxin-like protein.

[2] The marker for pancreatic cancer and intraductal papillary mucinous neoplasms according to the above [1], wherein the secretoglobin, family 1D, member 2 has any one of the following amino acid sequences (1) to (3).

(1) an amino acid sequence of SEQ ID NO: 1;

(2) an amino acid sequence corresponding to the amino acid sequence of SEQ ID NO: 1 having deletion, substitution and/or addition of 1 or more and 5 or less amino acid residues;

(3) an amino acid sequence having a sequence identity of 95% or more to the amino acid sequence of SEQ ID NO: 1.

[3] The marker for pancreatic cancer and intraductal papillary mucinous neoplasms according to the above [1] or [2], wherein the podocalyxin-like protein has any one of the following amino acid sequences (4) to (6).

(4) an amino acid sequence of SEQ ID NO: 2;

(5) an amino acid sequence corresponding to the amino acid sequence of SEQ ID NO: 2 having deletion, substitution and/or addition of 1 or more and 25 or less amino acid residues;

(6) an amino acid sequence having a sequence identity of 95% or more to the amino acid sequence of SEQ ID NO: 2.

[4] The marker for pancreatic cancer and intraductal papillary mucinous neoplasms according to any one of the above [1] to [3], further comprising CA 19-9.

[5] A kit for diagnosing pancreatic cancer and intraductal papillary mucinous neoplasms, comprising an antibody to one or more proteins selected from the group essentially consisting of secretoglobin, family 1D, member 2 and podocalyxin-like protein.

[6] The kit for diagnosing pancreatic cancer and intraductal papillary mucinous neoplasms according to the above [5], further comprising an antibody to CA19-9.

[7] A method for evaluating a metastasis of a pancreas cancer cell, comprising the step of measuring a concentration of one or more proteins selected from the group essentially consisting of secretoglobin, family 1D, member 2 and podocalyxin-like protein in a sample.

[8] A method for a diagnosing pancreatic cancer cell and an intraductal papillary mucinous neoplasms cell, comprising the step of measuring a concentration of one or more proteins selected from the group essentially consisting of secretoglobin, family 1D, member 2 and podocalyxin-like protein in a sample.

[9] The method according to the above [8], wherein the secretoglobin, family 1D, member 2 has any one of the following amino acid sequences (1) to (3).

(1) an amino acid sequence of SEQ ID NO: 1;
(2) an amino acid sequence corresponding to the amino acid sequence of SEQ ID NO: 1 having deletion, substitution and/or addition of 1 or more and 5 or less amino acid residues;
(3) an amino acid sequence having a sequence identity of 95% or more to the amino acid sequence of SEQ ID NO: 1.

[10] The method according to the above [8] or [9], wherein the podocalyxin-like protein has any one of the following amino acid sequences (4) to (6).

(4) an amino acid sequence of SEQ ID NO: 2;
(5) an amino acid sequence corresponding to the amino acid sequence of SEQ ID NO: 2 having deletion, substitution and/or addition of 1 or more and 25 or less amino acid residues;
(6) an amino acid sequence having a sequence identity of 95% or more to the amino acid sequence of SEQ ID NO: 2.

[11] The method according to any one of the above [8] to [10], further comprising CA 19-9.

[12] Use of one or more proteins selected from the group essentially consisting of secretoglobin, family 1D, member 2 and podocalyxin-like protein as a marker for pancreatic cancer and intraductal papillary mucinous neoplasms.

[13] The use according to the above [12], wherein the secretoglobin, family 1D, member 2 has any one of the following amino acid sequences (1) to (3).

(1) an amino acid sequence of SEQ ID NO: 1;
(2) an amino acid sequence corresponding to the amino acid sequence of SEQ ID NO: 1 having deletion, substitution and/or addition of 1 or more and 5 or less amino acid residues;
(3) an amino acid sequence having a sequence identity of 95% or more to the amino acid sequence of SEQ ID NO: 1.

[14] The use according to the above [12] or [13], wherein the podocalyxin-like protein has any one of the following amino acid sequences (4) to (6).

(4) an amino acid sequence of SEQ ID NO: 2;
(5) an amino acid sequence corresponding to the amino acid sequence of SEQ ID NO: 2 having deletion, substitution and/or addition of 1 or more and 25 or less amino acid residues;
(6) an amino acid sequence having a sequence identity of 95% or more to the amino acid sequence of SEQ ID NO: 2.

[15] The use according to any one of the above [12] to [14], wherein CA 19-9 is further used in combination.

Effect of the Invention

The marker for pancreatic cancer and intraductal papillary mucinous neoplasms according to the present invention contains the specific glycoproteins which accumulates in a lamellipodium characteristic of a pancreatic cancer cell. The inventor experimentally found that the glycoproteins are directly involved in the motility and invasion of a pancreatic cancer cell and are secreted outside the cell. Since a pancreatic cancer cell tends to metastasize and infiltrate in an early stage and the glycoproteins according to the present invention are involved in the motility and invasion of a pancreatic cancer cell, pancreatic cancer in an early stage may be detected by the glycoproteins. In addition, the inventor found that the glycoproteins are also useful for diagnosing intraductal papillary mucinous neoplasms. Thus, since the progresses of pancreatic cancer and whether there is intraductal papillary mucinous neoplasms or not can be evaluated by the marker for pancreatic cancer and intraductal papillary mucinous neoplasms according to the present invention, the marker may supersede a conventional tumor marker such as CA 19-9.

BRIEF DESCRIPTION OF THE DRAWINGS

FIG. 1 are photographs to demonstrate the results of immunostaining of SCGB1D2, PODXL and actin in a S2-013 cell.

FIG. 2 is an electrophoretic photograph to demonstrate the results of Western blotting to detect SCGB1D2, PODXL, CD63 and GAPDH in a S2-013 cell culture medium and the lysate thereof.

FIG. 3 is a graph to demonstrate the measurement results of SCGB1D2 concentrations in serum samples of the pancreatic cancer subject group and the control group.

FIG. 4 is a graph to demonstrate the measurement results of PODXL concentrations in serum samples of the pancreatic cancer subject group and the control group.

FIG. 5 is a graph to demonstrate the measurement results of SCGB1D2 concentrations in serum samples of the intraductal papillary mucinous neoplasms (IPMN) subject group and pancreatic cancer stages.

FIG. 6 is a graph to demonstrate the measurement results of PODXL concentrations in serum samples of the IPMN subject group and pancreatic cancer stages.

FIG. 7 is the sensitivity-specificity graph of measured values of SCGB1D2 and CA 19-9 between the pancreatic cancer subject group and the control group.

FIG. 8 is the sensitivity-specificity graph of measured values of PODXL and CA 19-9 between the pancreatic cancer subject group and the control group.

FIG. 9 is the sensitivity-specificity graph of measured values of SCGB1D2 and CA 19-9 between the pancreatic cancer subject group+the IPMN subject group and the control group.

FIG. 10 is the sensitivity-specificity graph of measured values of PODXL and CA 19-9 between the pancreatic cancer subject group+the IPMN subject group and the control group.

FIG. 11 is the sensitivity-specificity graph of measured values of SCGB1D2+PODXL and CA 19-9 alone between the pancreatic cancer subject group and the control group.

FIG. 12 is the sensitivity-specificity graph of measured values of SCGB1D2+PODXL+CA 19-9 and CA 19-9 alone between the pancreatic cancer subject group and the control group.

FIG. 13 is the sensitivity-specificity graph of measured values of SCGB1D2+PODXL and CA 19-9 alone between the pancreatic cancer subject group+the IPMN subject group and the control group.

FIG. 14 is the sensitivity-specificity graph of measured values of SCGB1D2+PODXL+CA 19-9 and CA 19-9 alone between the pancreatic cancer subject group+the IPMN subject group and the control group.

MODE FOR CARRYING OUT THE INVENTION

1. Marker for Pancreatic Cancer and IPMN

The marker for pancreatic cancer and IPMN according to the present invention is characterized in comprising one or more proteins selected from the group essentially consisting of secretoglobin, family 1D, member 2 and podocalyxin-like protein. Hereinafter, secretoglobin, family 1D, member 2 is abbreviated as "SCGB1D2", and podocalyxin-like protein is abbreviated as "PODXL". By using the proteins as the target to be detected, the progresses of pancreatic cancer and whether there is IPMN or not can be evaluated with high sensitivity and specificity.

The above-described term "sensitivity" in the present invention means a sensitivity to pancreatic cancer and IPMN, and means that, for example, when the above-described protein is used as the target to be detected, the probability that a pancreatic cancer patient and an IPMN patient are judged to be negative is low. The above-described term "specificity" in the present invention means a specificity to pancreatic cancer and IPMN, and means that while the amounts of the above-described proteins are highly correlated with whether there is pancreatic cancer and IPMN or not, the amounts of the above-described proteins are not correlated or has low relation with a benign disease and a cancer except for pancreatic cancer and IPMN.

The present invention marker is used for detecting pancreatic cancer. As the stage classification of pancreatic cancer, there are two classifications of a classification based on General Rules for the Study of Pancreatic Cancer by Japan Pancreas Society and an international UICC classification. In the present invention, the following classification based on General Rules for the Study of Pancreatic Cancer, which is generally used in Japan, is used.

TABLE 1

| Stage 0 | | Tumor is limited intraepithelially. |
|---|---|---|
| Stage I | | Tumor is limited to the pancreas, and the diameter is 2 cm or less. |
| Stage II | | Tumor is limited to the pancreas, but the diameter is larger than 2 cm, or Tumor metastasizes to surrounding lymph nodes. |
| Stage III | | Tumor spreads to outer side of the pancreas but does not metastasize to lymph nodes, or Tumor is limited to the pancreas but spreads in the pancreas and metastasizes to lymph nodes. |
| Stage IV | IVA | Tumor spreads to an organ or tissue around the pancreas, such as the stomach and spleen. |
| | IVB | Tumor metastasizes to an organ far away from the pancreas, such as the lungs and liver. |

In the present invention, "intraductal papillary mucinous neoplasms (IPMN)" is also the target to be detected. IPMN is also called as intraductal papillary mucinous adenoma, and is a precancerous lesion. The tumor produced by cancerization of IPMN may be defined as a cancer different from pancreatic cancer in some cases. When IPMN is left without treatment, IPMN cancerates. If such a cancerous IPMN cell infiltrates out of the pancreatic duct, a survival rate after 5 years is remarkably decreased. It is therefore needed to early detect and remove IPMN. It is however very difficult to detect IPMN by CA 19-9, which is a conventional pancreatic cancer marker. In the present invention, therefore, IPMN and intraductal papillary adenocarcinoma, which is a malignant tumor progressed from IPMN, are also included in the definition of pancreatic cancer as the target to be detected.

SCGB1D2 is a member of the lipophilin subfamily, which is included in the uteroglobin superfamily, and is an ortholog of prostatein, which is the major secretory glycoprotein derived from the rat prostate gland. Since human lipophilin is functionally equivalent to prostatein, it is thought that the lipophilin gene transcription is controlled by a steroid hormone.

PODXL is included in a member of CD34 and is a glycoprotein involved in the regulation of canceration in addition to the development and differentiation of a blood cell, and adhesion and morphogenesis of a cell. It has been reported that podocalyxin increases the malignant phenotype of a breast cancer cell and a prostate cancer cell and that podocalyxin may be used as a progressive marker; however, it has not been experimentally demonstrated that podocalyxin is useful as a marker of pancreatic cancer and IPMN as far as the inventor knows.

A pancreatic cancer cell has a characteristic that the cell is highly motile and easily metastasizes, and has lamellipodia, which is a protruding site involved in the motility of the cell. SCGB1D2 and PODXL according to the present invention are proteins which accumulate in lamellipodia of a pancreatic cancer cell. The inventor found that SCGB1D2 and PODXL are released from a pancreatic cancer cell. Since a pancreatic cancer cell exhibits motility and is infiltrative from the early stage and has lamellipodia, the pancreatic cancer marker according to the present invention may evaluate not only advanced pancreatic cancer but also early stage pancreatic cancer and pancreatic cancer immediately after metastasis with high sensitivity and specificity.

SCGB1D2 according to the present invention has the amino acid sequence of SEQ ID NO: 1, and PODXL according to the present invention has the amino acid sequence of SEQ ID NO: 2.

The above-described SCGB1D2 and PODXL may have a variation referred to as single nucleotide polymorphism in certain people, and such a variant protein is also useful as a marker for pancreatic cancer and IPMN. In other words, the markers having the following amino acid sequences are included in the present invention range.

Amino acid sequence (1): an amino acid sequence of SEQ ID NO: 1;

Amino acid sequence (2): an amino acid sequence corresponding to the amino acid sequence of SEQ ID NO: 1 having deletion, substitution and/or addition of 1 or more and 5 or less amino acid residues, and of a protein found in a body fluid of a pancreatic cancer patient and IPMN patient;

Amino acid sequence (3): an amino acid sequence having a sequence identity of 95% or more to the amino acid sequence of SEQ ID NO: 1, and of a protein found in a body fluid of a pancreatic cancer patient and IPMN patient;

Amino acid sequence (4): an amino acid sequence of SEQ ID NO: 2;

Amino acid sequence (5): an amino acid sequence corresponding to the amino acid sequence of SEQ ID NO: 2 having deletion, substitution and/or addition of 1 or more and 25 or less amino acid residues, and of a protein found in a body fluid of a pancreatic cancer patient and IPMN patient; Amino acid sequence (6): an amino acid sequence having a sequence identity of 95% or more to the amino acid sequence of SEQ ID NO: 2, and of a protein found in a body fluid of a pancreatic cancer patient and IPMN patient.

In the above-described amino acid sequence (2), the number of the deletion, substitution and/or addition is preferably not more than 4 or not more than 3, more preferably 1 or 2, and even more preferably 1. In the above-described amino acid sequence (5), the number of the deletion, substitution and/or addition is preferably not more than 20, not more than 15 or not more than 10, more preferably not more than 8, not more than 6, not more than 5 or not more than 4, and even more preferably 1 or 2.

With respect to the above-described amino acid sequence (3), the sequence identity is preferably not less than 96% or not less than 97%, more preferably 98% or more, and even more preferably 99% or more. With respect to the above-described amino acid sequence (6), the sequence identity is preferably not less than 96% or not less than 98%, more preferably not less than 99.0%, not less than 99.2% or not less than 99.5%, and even more preferably not less than 99.6% or not less than 99.8%.

With respect to the above-described amino acid sequences (2), (3), (5) and (6), the position and the presence or absence of the deletion, substitution and/or addition, and the sequence identity can be analyzed by directly comparing sequences, and can be specifically analyzed by using a commercially available sequence analysis software or the like.

Since there are few studies on a protein which accumulates in lamellipodia of a pancreatic cancer cell and it has not been reported that SCGB1D2 and PODXL according to the present invention have amino acid sequences other than the amino acid sequences of SEQ ID NO: 1 and SEQ ID NO: 2 respectively, it is preferred that the amino acid sequences of SCGB1D2 and PODXL according to the present invention are the amino acid sequences of SEQ ID NO: 1 and SEQ ID NO: 2 respectively.

It is preferred that the marker of pancreatic cancer and IPMN according to the present invention contains both of SCGB1D2 and PODXL. When the proteins are used as markers, the sensitivity and specificity can be improved more surely in comparison with the case where each protein alone is respectively used as a marker. It is more preferred that the marker of pancreatic cancer and IPMN according to the present invention contains CA 19-9 and SCGB1D2 or PODXL, and further SCGB1D2 and PODXL and CA19-9. The sensitivity and specificity can be improved more surely by such combinations.

2. Method for Diagnosing Pancreatic Cancer and IPMN

Next, each step of a method for diagnosing pancreatic cancer and IPMN in which the above-described marker for pancreatic cancer and IPMN is detected is described. It is thought that a pancreatic cancer cell which has metastasized from the pancreas is highly motile and infiltrative, has lamellipodia, which is necessary for such motility and invasion, and secretes SCGB1D2 and PODXL. Accordingly, the method for diagnosing pancreatic cancer according to the present invention is also effective as a method for evaluating the metastasis of a pancreatic cancer cell. For example, after a surgical surgery to remove pancreatic cancer, a pancreatic cancer cell which has already metastasized may be detected by the present invention method, even if the metastasis tissue is so small that the cell cannot be detected by a conventional pancreatic cancer marker.

(1) Step for Obtaining Sample

In this step, a sample is obtained from a subject. The sample means a body fluid such as blood, lymph and urine, and further a processed body fluid such as serum and blood plasma.

The sample of the present step is preferably a blood sample. Such a blood sample is the above-described blood itself, serum or blood plasma.

(2) Step for Measuring SCGB1D2 and/or PODXL

In this step, a concentration of one or more proteins selected from the group essentially consisting of SCGB1D2 and PODXL in a sample is measured.

An amount to be measure may be not only an absolute amount of SCGB1D2 and/or PODXL in a predetermined amount of a sample but also a concentration of SCGB1D2 and/or PODXL in a sample.

A measurement means is not particularly restricted as long as an amount of SCGB1D2 and/or PODXL in a sample can be measured by the means. For example, a spectrophotometric method such as ultraviolet absorption method, Bradford method, Lowry method and BCA method can be used. It is however preferred that ELISA method using an antibody which specifically binds to SCGB1D2 and/or PODXL is used, since the above-described spectrophotometric method may be affected by other components contained in a sample.

(3) Determination Step

It is determined whether there is pancreatic cancer and IPMN or not on the basis of an amount of the target protein measured in the above-described step. In fact, a sample is obtained from a pancreatic cancer patient, IPMN patient, non-pancreatic cancer patient, and further pancreatic cancer patients in various stages; amounts of SCGB1D2 and/or PODXL contained in the samples are preliminarily measured in the same condition; and the data are stored. A measurement result is compared with the stored data to determine whether there is pancreatic cancer and IPMN or not, the stage of pancreatic cancer, whether a pancreatic cancer cell metastasizes or not, or the like.

In addition, if an amount or concentration of CA 19-9 in a sample is further measured in the above-described measurement step (2) and the measurement value is considered in combination, the sensitivity and specificity for diagnosing pancreatic cancer and IPMN can be further improved.

3. Kit for Diagnosing Pancreatic Cancer and IPMN

The kit for diagnosing pancreatic cancer and IPMN according to the present invention is characterized in comprising an antibody to one or more proteins selected from the group essentially consisting of SCGB1D2 and PODXL. The kit can be used in the above-described present invention method using ELISA. Specifically, for example, a sample obtained from a subject is added to a plate to which an anti-SCGB1D2 antibody and/or an anti-PODXL antibody is bound and the plate is washed to specifically bind SCGB1D2 and/or PODXL in the sample. Then, SCGB1D2 and/or PODXL bound to the plate is detected by using a secondary antibody to which a marker group is bound, and an amount of SCGB1D2 and/or PODXL in the sample can be measured on the basis of the luminescence intensity by the marker group.

The kit for diagnosing pancreatic cancer and IPMN according to the present invention may further contain an antibody to CA 19-9. A diagnosis with higher sensitivity and specificity becomes possible by using such a kit, since CA 19-9 can be measured in addition to SCGB1D2 and/or PODXL.

The present application claims the benefit of the priority date of Japanese patent application No. 2015-242679 filed on Dec. 11, 2015. All of the contents of the Japanese patent application No. 2015-242679 filed on Dec. 11, 2015, are incorporated by reference herein.

EXAMPLES

Hereinafter, the examples are described to demonstrate the present invention more specifically, but the present invention is in no way restricted by the examples, and the examples can be appropriately modified to be carried out within a range which adapts to the contents of this specification. Such a modified example is also included in the technical range of the present invention.

Example 1: Identification of Pancreatic Cancer Cell Protein Usable as Pancreatic Cancer Marker The inventor has studied to elucidate the mechanism of the invasion and metastasis of a pancreatic cancer cell, and found and reported in Oncotarget, 5, pp. 6832-45 (2014) that insulin-like growth factor 2 mRNA-binding protein 3 (IGF2BP3) binds to the specific mRNA and is engaged on the regional translation of the mRNA in lamellipodia, which is a cell membrane projection. On the one hand, the inventor found but has not reported that the mRNAs of SCGB1D2 and PODXL are included in such mRNAs. Accordingly, the inventor studied the function of SCGB1D2 and PODXL.

First, human pancreatic cancer cell line S2-013 was subjected to immunocytostaining in order to investigate whether or not SCGB1D2 and PODXL which were proteins produced by local translation were localized to lamellipodia of a pancreatic cancer cell. The result is shown in FIG. 1. As shown in FIG. 1, SCGB1D2 and PODXL are present especially in lamellipodia in which actin was polymerized.

The above two proteins are glycoproteins, and glycoprotein is a secreted protein or tends to be localized frequently at a cell membrane. The inventor therefore examined by Western blot method whether or not the proteins were secreted from a pancreatic cancer cell line S2-013 into the culture medium. Specifically, the sample was obtained by recovering the culture supernatant of S2-013 cell, removing the cell components with centrifugation, and concentrating the residue, and was analyzed by Western blot using an anti-SCGB1D2 antibody and an anti-PODXL antibody. In addition, the S2-013 cell lysate was similarly analyzed. Furthermore, Western blot using an antibody to CD63, which is a secreted protein, and an antibody to GAPDH, which is an intracellular non-secretory protein, was also conducted. The result is shown in FIG. 2. As FIG. 2, it was confirmed that SCGB1D2 and PODXL were secreted extracellularly as CD63, which is a secreted protein. Also, it was confirmed that the culture supernatant of S2-013 cell could be surely recovered, since the band of GAPDH could not be recognized in the culture supernatant.

From the above results, it was found that SCGB1D2 and PODXL which accumulate in lamellipodia are secreted from a pancreatic cancer. The inventor hypothesized that SCGB1D2 and PODXL are released into tumor tissue interstitium from a pancreatic cancer cell having lamellipodia in human pancreatic cancer tissue and infiltrates in intratumoral blood vessel. In order to prove this hypothesis, a clinical study was carried out to quantitatively measure SCGB1D2 and PODXL by using serum of pancreatic cancer cases.

Example 2: Diagnosis Test (1) Selection of Subject

The test was conducted on the 23 pancreatic cancer cases including 1 case of stage I pancreatic cancer, 5 cases of stage III pancreatic cancer and 17 cases of stage IV advanced pancreatic cancer, and 11 cases of benign IPMN (intraductal papillary mucinous neoplasm), which cases were diagnosed in the gastroenterological medicine of Kochi Medical School Hospital. As IPMN cases, patients who had no history of cancer and who had not undergone surgery were subjected. As control, 51 cases of patients who were visiting the gastroenterological medicine of Kochi Medical School Hospital and who did not have pancreatic disease but had chronic hepatitis, colonic polyps or gastric polyps were applied. The inventor and two supervisory doctors of Japanese Gastroenterology Society who diagnosed a pancreatic disease explained to the subjects with using the explanatory document approved by the clinical trial committee of Kochi Medical School, and registered the subjects as the clinical cases after obtaining the written agreement from the patients themselves. After collecting blood from each subject, serum was quickly separated, and 0.2 mL of each serum was poured into 1.5 mL vessel. The serum was stored in a dedicated freezer at −20° C., and strictly controlled until the measurement.

The average age and standard deviation of the pancreatic cancer subjects were respectively 71.70 years old and 8.91, and the average age and standard deviation of the control subjects were respectively 65.66 years old and 13.35. Pancreatic cancer is common in elderly people, and the average age of pancreatic cancer cases tended to be higher in this clinical trial; however, there was not significant difference between the two groups by Student's t-test at $P=0.052$. In addition, the pancreatic cancer subjects contained 12 female subjects and 11 male subjects, and the control subjects contained 31 female subjects and 20 male subjects. $\chi^2$ test was conducted with respect to sex, and there was not significant difference between the two groups at $P=0.24$. The average age and standard deviation of the IPMN case subjects were respectively 65.85 years old and 7.88, and there was not significant difference between the IPMN group and control group by t-test at $P=0.055$. The IPMN case subjects contained 4 female subjects and 7 male subjects, and there was not significant difference between the IPMN group and control group by $\chi^2$ test at $P=0.158$.

(2) Measurement of Concentrations of SCGB1D2 and PODXL in Serum

The concentrations of SCGB1D2 and PODXL in the serum samples of the subjects were measured by using commercially available sandwich ELISA kit ("SCGB1D2 ELISA kit, CSB-EL020814HU" manufactured by CUSABIO and "ELISA kit for PODXL, SEA768Hu" manufactured by CLOUD-CLONE).

Specifically, in the case of SCGB1D2, 100 μL of the serum of the subject was added to each well of the microtiter plate of the kit, and the mixture was reacted at 37° C. for 2 hours. Then, 100 μL of biotin-labeled antibody was added to each well, and the mixture was reacted at 37° C. for 1 hour. Next, each well was washed 3 times with PBS. Further, after 100 μL of HRP-avidin as a labelling enzyme was added to each well and the mixture was reacted at 37° C. for 1 hour, the well was washed 5 times with PBS. Then, 90 μL of TMB solution as a color developing agent was added to each well, and the mixture was reacted at room temperature for 15 minutes. In order to stop the reaction, 50 μL of a reaction terminator solution was added, and an absorbance at 450 nm was measured. The concentration of SCGB1D2 in serum was obtained by comparing the measurement result with a calibration curve.

In the case of PODXL, 100 μL of the serum of the subject was added to each well of the microtiter plate of the kit, and the mixture was reacted at 37° C. for 2 hours. Then, 100 μL of Detection Reagent A was added to each well, and the mixture was reacted at 37° C. for 1 hour. Next, each well was washed 3 times with PBS. Further, after 100 μL of Detection Reagent B as a labelling enzyme was added to each well and the mixture was reacted at 37° C. for 30 minutes, the well was washed 5 times with PBS. Then, 90 μL of Substrate solution as a color developing agent was added to each well, and the mixture was reacted at room temperature for 15 minutes. In order to stop the reaction, 50 μL of a reaction terminator solution was added, and an absorbance at 450 nm was measured. The concentration of PODXL in serum was obtained by comparing the measurement result with a calibration curve.

In addition, the concentration of CA 19-9 as a conventional pancreatic cancer marker in serum was similarly measured for comparison by using commercially available ELISA kit ("TM-CA 19-9 ELISA KIT, EIA5069" manufactured by DRG International).

(3) Consideration of Measurement Result

The result of SCGB1D2 is shown in FIG. 3, and the result of PODXL is shown in FIG. 4. The median value of the SCGB1D2 concentration in the pancreatic cancer subject group serum was 238.872 ng/mL (interquartile range: 599.602), and the median value in the control subject group serum was 71.091 ng/mL (interquartile range: 91.434). The median value of the PODXL concentration of the pancreatic cancer subject group serum was 8.738 ng/mL (interquartile range: 6.284), and the median value in the control subject group serum was 0.093 ng/mL (interquartile range: 0.705). The concentrations of SCGB1D2 and PODXL were respectively subjected to Mann-Whitney U test between the pancreatic cancer subject group and the control subject group; as a result, significant differences were recognized at P<0.001 in terms of both.

With respect to the results of each stage of pancreatic cancer and the result of IPMN (intraductal papillary mucinous neoplasm) group, the result of SCGB1D2 is shown in FIG. 5 and the result of PODXL is shown in FIG. 6. It was recognized that SCGB1D2 and PODXL were increased in any stages of I, III and IV of pancreatic cancer in comparison with the control cases. The median value of the SCGB1D2 concentration in the IPMN group serum was 132.554 ng/mL (interquartile range: 199.544), the median value of the PODXL concentration was 9.199 ng/mL (interquartile range: 4.872), and it was recognized that SCGB1D2 and PODXL in the IPMN group serum were increased in comparison with the values in the control subject groups serum.

The sensitivity-specificity graphs of the measurement results of SCGB1D2 and PODXL are respectively shown as FIG. 7 and FIG. 8. In the sensitivity-specificity graph, it is demonstrated that when the position of the graph is placed lefter and upper, in other words, when the area under the curve (AUC) is larger, both of sensitivity and specificity of a pancreatic cancer marker are more excellent. The inventor therefore measured AUC between the pancreatic cancer case and control in each graphs; as a result, the AUC value of SCGB1D2 was similar to that of CA 19-9 and the AUC value of PODXL was significantly larger than that of CA 19-9 at P=0.00405, as the AUC value of SCGB1D2 was 0.76 (95% CI 0.609-0.91), the AUC value of PODXL was 0.973 (95% CI 0.943-1) and the AUC value of CA 19-9 was 0.802 (95% CI 0.693-0.912). As the above, it was demonstrated that the diagnostic ability of PODXL is significantly superior to that of CA 19-9 in terms of both of sensitivity and specificity, and SCGB1D2 has a similar diagnostic ability to CA 19-9.

As the above-described results, it was demonstrated that SCGB1D2 and PODXL can be used as a diagnostic marker for both of pancreatic cancer and IPMN; therefore, it was needed to compare the pancreatic cancer case+IPMN case with control in addition to the comparison between the pancreatic cancer case and control. The sensitivity-specificity graphs of the case where the pancreatic cancer case+ IPMN case was compared with control are respectively shown as FIG. 9 and FIG. 10. In addition, AUC between the pancreatic cancer case+IPMN case and control was measured in each graph; as a result, the AUC value of SCGB1D2 was similar to that of CA 19-9, and there was not significant difference between PODXL and CA 19-9 at P=0.178 but the diagnostic ability of PODXL might be superior to that of CA 19-9, as the AUC value of SCGB1D2 was 0.748 (95% CI 0.599-0.896), the AUC value of PODXL was 0.889 (95% CI 0.823-0.956) and the AUC value of CA 19-9 was 0.799 (95% CI 0.689-0.909). When the cutoff values of SCGB1D2 and PODXL were respectively set at 185.58 and 2.68, the diagnostic sensitivity and specificity of SCGB1D2 for pancreatic cancer+IPMN were respectively 65.2% and 90.3%, and the diagnostic sensitivity and specificity of PODXL for pancreatic cancer+IPMN were respectively 100% and 72.6%. As the above results, it was demonstrated that the diagnostic ability of PODXL for pancreatic cancer+IPMN may be superior to that of CA 19-9, and SCGB1D2 has a similar diagnostic ability to CA 19-9.

In addition, the combination of SCGB1D2 and CA 19-9 and the combination of PODXL and CA 19-9 were analyzed by the Spearman rank correlation coefficient test in order to test the relevance in each combination. As a result, the concentrations of SCGB1D2 and PODXL in serum did not correlate with the concentration of CA 19-9 in serum as r=0.212 and P=0.319 in the case of the combination of SCGB1D2 and CA 19-9, and r=0.144 and P=0.498 in the case of the combination of PODXL and CA19-9. Thus, since SCGB1D2 and PODXL do not have relevance with CA 19-9, the sensitivity and specificity of CA 19-9 alone for diagnosis of pancreatic cancer may be improved by combining SCGB1D2 and PODXL with CA 19-9. The effect by the combination of SCGB1D2 and PODXL on pancreatic cancer diagnosis was examined by measuring the AUC value of the sensitivity-specificity graph. The AUC value of the case where SCGB1D2 and PODXL were combined was 0.982 (95% CI 0.845-0.963), and both of the sensitivity and specificity were significantly superior to CA 19-9 alone (P=0.0017, FIG. 11). As described above, the diagnostic ability of PODXL alone for pancreatic cancer is very excellent; in addition, the AUC value further became large by combining PODXL with SCGB1D2. In addition, when SCGB1D2 and PODXL were combined with CA 19-9, both of sensitivity and specificity were significantly superior to CA 19-9 alone (P=0.0013, FIG. 12) as the AUC was 0.983 (95% CI 0.962-1). On the one hand, since the diagnostic ability of the combination of SCGB1D2 and PODXL and CA 19-9 was almost not improved in comparison with the combination of SCGB1D2 and PODXL, it was clarified that PODXL alone or the combination of PODXL and SCGB1D2 is useful for diagnosing pancreatic cancer.

Then, the effect by the combination SCGB1D2 and PODXL on the diagnosis of pancreatic cancer+IPMN was studied by measuring the AUC value of the sensitivity-specificity graph. The AUC value of the case where SCGB1D2 and PODXL were combined was 0.910 (95% CI 0.851-0.969), and both of sensitivity and specificity tended to be superior to CA 19-9 alone (P=0.073, FIG. 13). As described above, the diagnostic ability of PODXL alone for pancreatic cancer+IPMN is very excellent; in addition, the AUC value further became large by combining PODXL with SCGB1D2. Furthermore, the AUC value of the case where SCGB1D2 and PODXL were combined with CA 19-9 was 0.922 (95% CI 0.868-0.976), and both of sensitivity and specificity were superior to CA 19-9 alone (P=0.029, FIG. 14). Accordingly, the combination of PODXL and SCGB1D2 and CA 19-9 is a serum marker for diagnosing pancreatic cancer+IPMN with high sensitivity and specificity.

The invention claimed is:

1. A method for detecting a concentration of secretoglobin, family 1D, member 2 protein and podocalyxin-like protein in a blood sample from a human subject suspected of having pancreatic cancer or intraductal papillary mucinous neoplasms comprising:
   (a) contacting the secretoglobin, family 1D, member 2 protein and the podocalyxin-like protein in the blood sample with antibodies to the secretoglobin, family 1D, member 2 protein and the podocalyxin-like protein; and
   (b) measuring a concentration of the secretoglobin, family 1D, member 2 protein and the podocalyxin-like protein,
   wherein the secretoglobin, family 1D, member 2 protein has the amino acid sequence of SEQ ID NO: 1, and the podocalyxin-like protein has the amino acid sequence of SEQ ID NO: 2.

2. The method according to claim 1, wherein the method further comprises determining a concentration of CA 19-9 in a blood sample from the subject by the same way as in the steps (a) and (b) using an antibody to CA 19-9.

3. The method according to claim 2, wherein the blood sample is serum.

4. The method according to claim 1, wherein the blood sample is serum.

5. The method of claim 1, wherein the measuring is performed with a method selected from the group consisting of a spectrophotometric method, Bradford method, Lowry method, ELISA method, and BCA method.

* * * * *